United States Patent [19]

Tanaka et al.

[11] Patent Number: 4,632,879
[45] Date of Patent: Dec. 30, 1986

[54] MOISTURE SENSOR

[75] Inventors: Junichi Tanaka, Tenri; Hisatoshi Furubayashi, Yamatokoriyama; Masanori Watanabe, Tenri; Masaya Hijikigawa, Yamatokoriyama, all of Japan

[73] Assignee: Sharp Kabushiki Kaisha, Japan

[21] Appl. No.: 604,389

[22] Filed: Apr. 27, 1984

[30] Foreign Application Priority Data

Apr. 30, 1983 [JP] Japan ................... 58-77802

[51] Int. Cl.⁴ .............................. B32B 27/30
[52] U.S. Cl. .................... 428/522; 428/913; 428/328; 73/336.5
[58] Field of Search ............... 428/328, 463, 522, 913; 73/336.5

[56] References Cited

U.S. PATENT DOCUMENTS

| 3,983,527 | 9/1976 | Ohsato et al. | 428/328 |
| 4,442,422 | 4/1984 | Murata et al. | 73/336.5 |
| 4,496,931 | 1/1985 | Watanabe et al. | 73/336.5 |
| 4,528,543 | 7/1985 | Miyoshi et al. | 428/210 |

Primary Examiner—George F. Lesmes
Assistant Examiner—P. R. Schwartz
Attorney, Agent, or Firm—Keil & Weinkauf

[57] ABSTRACT

A moisture sensor comprising a substrate, a bottom electrode formed on said substrate, a moisture sensitive film formed on said bottom electrode and a moisture permeable electrode formed on said moisture sensitive film, said moisture sensitive film being formed by heat-treating polyvinyl alcohol, thereby exhibiting a moisture sensitive characteristic which has a linear relationship between the impedance and the relative humidity.

2 Claims, 5 Drawing Figures

FIG. 1A
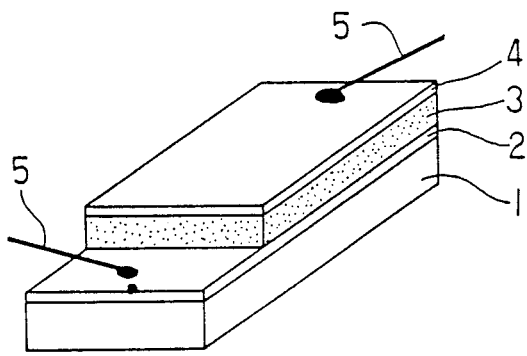
FIG. 3A
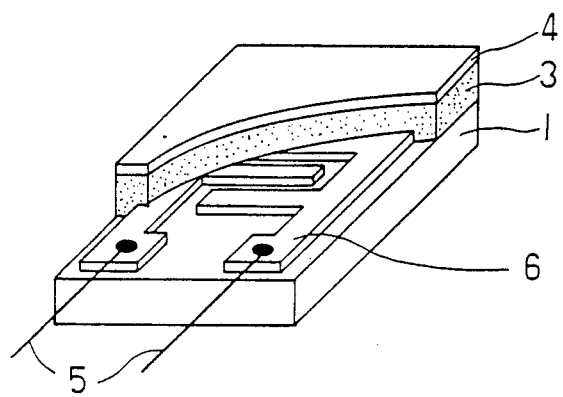
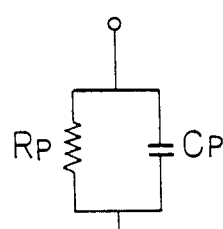
FIG. 1B
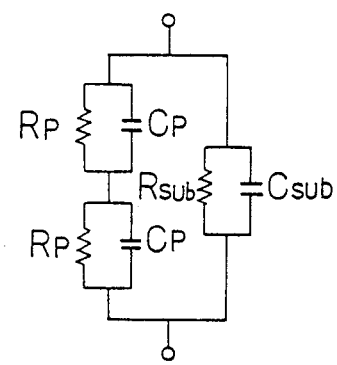
FIG. 3B

MOISTURE SENSOR

BACKGROUND OF THE INVENTION

1. Field of the Invention

The present invention relates to a moisture sensor having a polymer film, which detects variation of humidity in the atmosphere with a variation in the impedance of the polymer film.

2. Description of the Prior Art

As a moisture sensor wherein an impedance varies depending upon a variation of humidity in the atmosphere, there have been, for example, a moisture sensor having a sintered body of metal oxides such as tin oxide($SnO_2$), or a metal oxide film; a moisture sensor having a hydrophilic polymer film; a moisture sensor having an electrolyte salt such as lithium chloride(LiCl); and a moisture sensor having a hygroscopic resin or polymer film in which conductive particles or fibers such as carbon are dispersed.

While a moisture sensor containing a metal oxide film or a hydrophilic film has a wide moisture-sensitivity range, its resistance varies exponentially responding to relative humidity in the atmosphere. A moisture sensor having an electrolyte salt such as lithium chloride detects only humidity in a narrow range so that when it is allowed to stand in a high humidity atmosphere for a long period of time, the electrolyte salt therein is eluted or diluted resulting in deterioration of the moisture sensitive characteristic of the sensor, and accordingly it cannot be used for determination of high humidity. Also, a moisture sensor having a hygroscopic resin or the like, in which conductive particles or fibers are dispersed, cannot detect a humidity in a wide range because it exhibits a steep variation of the resistance thereof in a high humidity atmosphere, while it is not sensitive to low humidity.

SUMMARY OF THE INVENTION

The moisture sensor of this invention which overcomes the above-discussed disadvantages of the prior art, comprises a substrate, a bottom electrode formed on said substrate, a moisture sensitive film formed on said bottom electrode and a moisture permeable electrode formed on said moisture sensitive film, said moisture sensitive film being formed by heat-treating polyvinyl alcohol.

The moisture sensitive film is prepared by heat-treating polyvinyl alcohol at a temperature ranging from 150° C. to 250° C.

Thus, the invention described herein makes possible the objects of providing a novel and useful moisture sensor, the impedance of which is substantially represented by a first-order function of the relative humidity ranging from 0% to 90%, that is, an approximately linear relationship exists between the impedance and the relative humidity; providing a compact and inexpensive moisture sensor which does not require a logarithm transducer; providing a moisture sensor which is excellent in water resistance; providing a moisture sensor which is excellent in response; providing a moisture sensor having a small hysteresis of the moisture sensitive characteristic curve; providing a moisture sensor which is easily manufactured; and providing a moisture sensor which is uniform in quality because it is constituted by components consisting of simple composition.

BRIEF DESCRIPTION OF THE DRAWINGS

This invention may be better understood and its numerous objects and advantages will become apparent to those skilled in the art by reference to the accompanying drawings as follows:

FIG. 1(A) is a perspective view of a moisture sensor according to this invention.

FIG. 1(B) is an equivalent network of the moisture sensor shown in FIG. 1(A).

FIG. 3(A) is a partly sectional perspective view of another moisture sensor according to this invention.

FIG. 3(B) is an equivalent network of the moisture sensor shown in FIG. 3(A).

DESCRIPTION OF THE PREFERRED EMBODIMENTS

Figure 2:
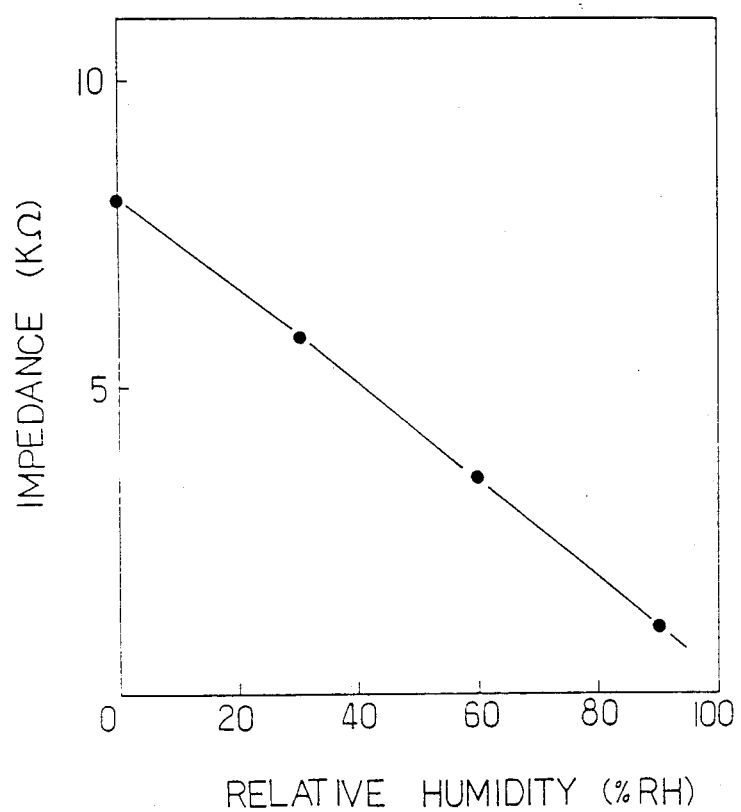
FIG. 2 is a graph of the moisture sensitive characteristic of the moisture sensor shown in FIG. 1(A).

The arrangement, function and effects of the invention will now be described with reference to the drawings showing embodiments of the invention. The following illustrates the most typical examples, but it is to be understood that these are not intended to limit the scope of the invention and that changes and modifications thereof are within the technical scope of the invention.

FIG. 1(A) shows a moisture sensor according to this invention, wherein on a substrate 1 made of an insulator such as glass, alumina or the like, or a semiconductor such as silicone or the like, a metal conductive film such as gold or the like is formed by a vacuum evaporation technique or a spattering method to form a bottom electrode 2. As the substrate 1 a metal board may be used, which serves as a bottom electrode.

Then, a moisture sensitive film 3 is formed on the bottom electrode 2 in the following processes:

Polyvinyl alcohol, dissolved in a solvent such as water or polyhydric alcohol, is coated on the bottom electrode 2 by a spin casting method, a printing technique or an immersion method to form a film of desired thickness on the bottom electrode 2, which is then dried by a ventilation process followed by a heat treatment at a temperature ranging from 150° C. to 250° C. with the formation of the moisture sensitive film 3. Generally, polyvinyl alcohol is a water-soluble and crystallizable polymer and tends to crystallize as the temperature of the heat treatment rises. Thus, when polyvinyl alcohol is heat-treated at 150° C. or higher, it becomes sufficiently water-resistant for practical purposes such that it is not eluted due to a dew condensation from the final product, the moisture sensitive film. However, it starts to be decomposed at a heat-treating temperature of 200° C. or higher and is vigorously decomposed at 250° C. or higher thereby losing its inherent moisture sensitive characteristic. For these reasons, in order to prepare a water-resistant moisture sensitive film, polyvinyl alcohol is required to be subjected to a heat treatment at a temperature ranging from 150° C. to 250° C.

Polyvinyl alcohol has a very high resistance to oils and chemicals, for example, animal oils, mineral oils, aliphatic hydrocarbons, aromatic hydrocarbons, ethers, esters, ketones, etc. The moisture sensitive film 3 according to this invention is formed by high crystallizable polyvinyl alcohol which is heat treated at around 200° C., and operates stably even under severe conditions of use.

On the moisture sensitive film 3, a moisture permeable conductive film made of gold or the like is formed by a vacuum evaporation technique or a spattering method to form an upper electrode 4. A lead wire 5 is connected to the bottom electrode 2 and another lead wire 5 is connected to the upper electrode 4 thereby constituting a pair of detecting electrodes, through which an electric current flows to determine variation of the impedance of the moisture sensitive film 3.

FIG. 1(B) shows an equivalent network of the moisture sensor shown in FIG. 1(A), wherein the moisture sensitive film 3 has a capacity component Cp and a resistance component Rp such that the impedance varies responding to variation of the humidity in the atmosphere.

A process for the production of the above-mentioned moisture sensor and an operation characteristic of the same will be described in detail below:

A gold film is formed as a bottom electrode 2 by means of a vacuum evaporation technique on the substrate 1. The formed gold bottom electrode film has a thickness of about 2000 Å. On the bottom electrode 2, an aqueous solution of polyvinyl alcohol is coated with a thickness of about 2 μm by a spin casting method, dried by a ventilation process and then heat-treated at 180° C. for 30 minutes to form the moisture sensitive film 3. An upper electrode 4 made of gold is disposed with a thickness of 200 Å on the moisture sensitive film 3 by a vacuum evaporation technique. The upper electrode 4 and the bottom electrode 2 are connected to a detecting circuit by lead wires 5, resulting in the desired moisture sensor.

FIG. 2 shows a characteristic curve at a time when alternating current having a voltage 0.1 V and a frequency of 10 KHz is applied to the moisture sensor at a temperature of 25° C. It indicates that a linear relationship exists between the impedance and the relative humidity ranging from 0% to 90% of the relative humidity. The characteristic exhibiting such a linear relationship in the moisture sensor according to this invention will be explained as follows: The above-mentioned equivalent network of the moisture sensor, as shown in FIG. 1(B), has a resistance component Rp and a capacity component Cp which are parallelly connected to a detecting circuit. In a low or ordinary humidity atmosphere, variation of the impedance of the moisture sensitive film 3 is substantially controlled by variation of the capacity component Cp and there is a linear relationship between the impedance due to the capacity and the relative humidity. In a high humidity atmosphere, variation of the impedance is substantially controlled by variation of the resistance component Rp and the impedance due to the capacity, represented by $1/(2\pi fCp)$, depends upon the frequency. The impedance due to resistance, however, does not depend upon the frequency. For these reasons, if a proper frequency is chosen, a desired moisture sensitive characteristic, which exhibits a linear relationship between the impedance and the relative humidity ranging from 0% to 90% of the relative humidity, will be attained. Even though the area of the electrode and/or the thickness of the moisture sensitive film are changed, the above-discussed characteristic will be unaffected.

FIG. 3 shows an alternative structure of the moisture sensor, wherein the moisture sensitive film 3 is formed on a pair of comb-shaped electrodes 6 disposed on the insulative substrate 1 and a moisture permeable conductive film 4 is disposed on the moisture sensitive film 3. An equivalent network of this moisture sensor in FIG. 3(A) as shown in FIG. 3(B), wherein the references Rsub and Csub are a resistance component of the substrate and a capacity component of the substrate, respectively. The synthesized impedance due to the resistance component Rp and the capacity component Cp of the moisture sensitive film depends upon the thickness of the moisture sensitive film and the area of the electrodes. Also, the synthesized impedance due to the resistance component Rsub and the capacity component Csub of the substrate depends upon the material of the substrate and the shape of the electrodes. For these reasons, if the thickness of the moisture sensitive film, the material of the substrate, and/or the area and the shape of the electrodes is chosen such that the synthesized impedance due to Rsub and Csub becomes significantly higher than the synthesized impedance due to Rp and Cp, the synthesized impedance due to Rsub and Csub may be negligible and the synthesized impedance alone due to Rp and Cp becomes effective in the equivalent network. Such a synthesized impedance due to Rp and Cp corresponds to the fact that the equivalent network shown in FIG. 3(B) is composed of a series of Rp and Cp resulting in the twice synthesized impedance produced by the equivalent network shown in FIG. 1(B). It means that the moisture sensor shown in FIG. 3 also exhibits such a moisture sensitive characteristic having a linear relationship between the impedance and the relative humidity as in the moisture sensor shown in FIG. 1.

It is understood that various other modification will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A moisture sensor comprising a substrate, a bottom electrode formed on said substrate, a moisture sensitive film formed on said bottom electrode and a moisture permeable electrode formed on said moisture sensitive film, said moisture sensitive film being formed by high crystallizable polyvinyl alcohol which is heat treated thereby attaining a linear relationship between the impedance and the relative humidity ranging from 0% to 90% of the relative humidity.

2. A moisture sensor according to claim 1, wherein said moisture sensitive film is prepared by heat-treating polyvinyl alcohol at a temperature ranging from 150° C. to 250° C.

* * * * *